(12) United States Patent
Moteki

(10) Patent No.: US 6,514,213 B1
(45) Date of Patent: Feb. 4, 2003

(54) EARPIECE ASSEMBLY FOR A STETHOSCOPE

(75) Inventor: Takashi Moteki, Kanra-machi (JP)

(73) Assignee: Moteki Industries, Inc., Gumma (JP)

( * ) Notice: Subject to any disclaimer, the term of this patent is extended or adjusted under 35 U.S.C. 154(b) by 0 days.

(21) Appl. No.: 09/678,403

(22) Filed: Oct. 3, 2000

(51) Int. Cl.$^7$ ................................................ A61B 5/25
(52) U.S. Cl. .......................... 600/528; 181/131; 381/67
(58) Field of Search .................. 181/126, 130, 181/131, 134, 135; 381/67; 600/528, 508, 509, 513, 586; D24/134

(56) References Cited

U.S. PATENT DOCUMENTS 3,621,845 A * 11/1971 Oates .................... 128/2.05 S
3,710,888 A * 1/1973 Peart ............................ 181/24
5,774,563 A * 6/1998 DesLauriers et al. ......... 381/67

* cited by examiner

Primary Examiner—Jeffrey R. Jastrazab
Assistant Examiner—Frances P. Oropeza
(74) Attorney, Agent, or Firm—Jim Zegeer

(57) ABSTRACT

An earpiece assembly for use in a stethoscope having a pipe member includes a connector having a distal end coupled to the pipe member and a proximal end, a bushing having a distal end rotatably coupled to the proximal end of the connector and a proximal end, and an earpiece having a sound path and being coupled to the proximal end of the bushing. The earpiece assembly may further include a bearing for rotatably coupling the connector and the bushing. The earpiece assembly provides a stethoscope that produces less undesired noise and prevents an injury to user's ears during the operation of the stethoscope.

14 Claims, 5 Drawing Sheets

EARPIECE ASSEMBLY FOR A STETHOSCOPE

CROSS REFERENCE TO RELATED APPLICATION

The present application claims foreign priority from a Japanese patent application, JP Hei 11-284901, the content of which is expressly incorporated herein by its entirety.

BACKGROUND OF THE INVENTION

1. Field of the Invention

The present invention relates to a stethoscope often used to monitor physiological sounds. More particularly, the invention is directed to an earpiece assembly for a stethoscope that facilitates the operation of the stethoscope.

2. Description of the Related Art

A stethoscope is a diagnostic instrument often used in medical practice for listening physiological sounds, such as heart and respiratory sounds. As shown in FIG. 3, a stethoscope generally includes a sound-receiving portion 50 to be pressed against the body. Sound-receiving portion 50 is acoustically coupled to earpieces 54, which are designed to fit into ears of a stethoscope user while listing to the sound of the patient body. For the purpose of this discussion, the term "distal" refers to the direction of the patient body and the term "proximal" refers to the direction of the stethoscope user. Sound-receiving portion 50 has a diaphragm member and is acoustically connected to the distal end of an elastic tubular transmission member 51. Tubular member 51, often made of resin, bifurcates into two bifurcated transmission portions 52. A pipe member 53, often made of a metal, is acoustically connected to the proximal end of each of bifurcated transmission portions 52. Each of earpieces 54 is attached to the proximal end of pipe member 53. The stethoscope has a sound passage extending from sound-receiving portion 50 to each of earpieces 54. The stethoscope also has a bridge member 55 attached to pipe members 53. Bridge member 55 is biased to prevent pipe members 53 from spreading apart more than necessary and to keep earpieces 54 in user's ears during the operation of the stethoscope.

FIG. 4 illustrates an earpiece assembly typically used in the stethoscope. The earpiece assembly includes earpiece 54 having a cylindrical portion 58 projecting from an earpiece body, and a connector 57 that has an opening with a screw surface 56. Connector 57 often has a cylindrical shape and is made of resin. Pipe member 53 has a screw portion 60 to be screwed to screw surface 56 of connector 57.

As shown in FIG. 5, connector 57 is inserted in cylindrical portion 58 of earpiece 54, and is secured in cylindrical portion 58 by caulking the end 59 of the cylindrical portion 58. Pipe member 53 is securely screwed into the opening of connector 57.

This structure of a stethoscope, however, is associated with common problems. Due to the manner in which earpiece 54 is secured to pipe member 53 in the stethoscope, earpiece 54 rotates in the user's ear when pipe member 53 moves during the operation of the stethoscope. Such rotation of earpiece 54 in the use's ear produces undesired frictional noise, making difficult to monitor the sounds from the patient. Moreover, the movement of pipe members 53 in the stethoscope is directly transferred to earpiece 54. When pipe member 53 is pulled, therefore, earpiece 54 is often pulled out of the user's ear. Such movement of earpiece 54 disturbs the operation of the stethoscope and may results in an injury to the user's ear.

SUMMARY OF THE INVENTION

This invention provides a stethoscope that addresses the aforementioned problems associated with the conventional stethoscope. One object of the invention is to provide a stethoscope having an earpiece assembly to produce less undesired noise and to prevent an injury to user's ears during the operation of the stethoscope.

Additional objects and advantages of the invention will be set forth in part in the following description, or may be learned by practice of the invention. The advantages and purpose of the invention will be realized and attained by the elements and combinations particularly pointed out in the appended claims.

To attain the advantages and in accordance with the purposes of the invention, as embodied and broadly described herein, the invention comprises an earpiece assembly for use in a stethoscope having a pipe member. The earpiece assembly includes a connector having a distal end coupled to the pipe member and a proximal end, a bushing having a distal end rotatably coupled to the proximal end of the connector and a proximal end, and an earpiece having a sound path and being coupled to the proximal end of the bushing.

In another aspect of the invention, the objects and advantages of the invention are attained by a stethoscope including a sound-receiving portion, a tubular member acoustically coupled to the sound-receiving portion, an earpiece assembly acoustically coupled to the tubular member. The earpiece assembly has a connector having a distal end coupled to the pipe member and a proximal end, a bushing having a distal end rotatably coupled to the proximal end of the connector and a proximal end, and an earpiece having a sound path and being coupled to the proximal end of the bushing.

Both the foregoing general description and the following detailed description are exemplary and explanatory only and are not restrictive of the invention, as claimed.

BRIEF DESCRIPTION OF THE DRAWINGS

The accompanying drawings, which are incorporated in this specification, illustrate one embodiment of the invention and together with the description, serve to explain the principles of the invention. In the drawings.

DESCRIPTION OF THE PREFERRED EMBODIMENTS

Reference will now be made in detail to the present preferred embodiment of the invention, an example of which is illustrated in the accompanying drawings. Wherever possible, the same reference numbers will be used throughout the drawings to refer to the same or like parts.

In accordance with the invention, a stethoscope having a pipe member is provided with an earpiece assembly including a connector having a distal end coupled to the pipe member and a proximal end, a bushing having a distal end rotatably coupled to the proximal end of the connector and a proximal end, and an earpiece having a sound path and being coupled to the proximal end of the bushing.

Figure 1:
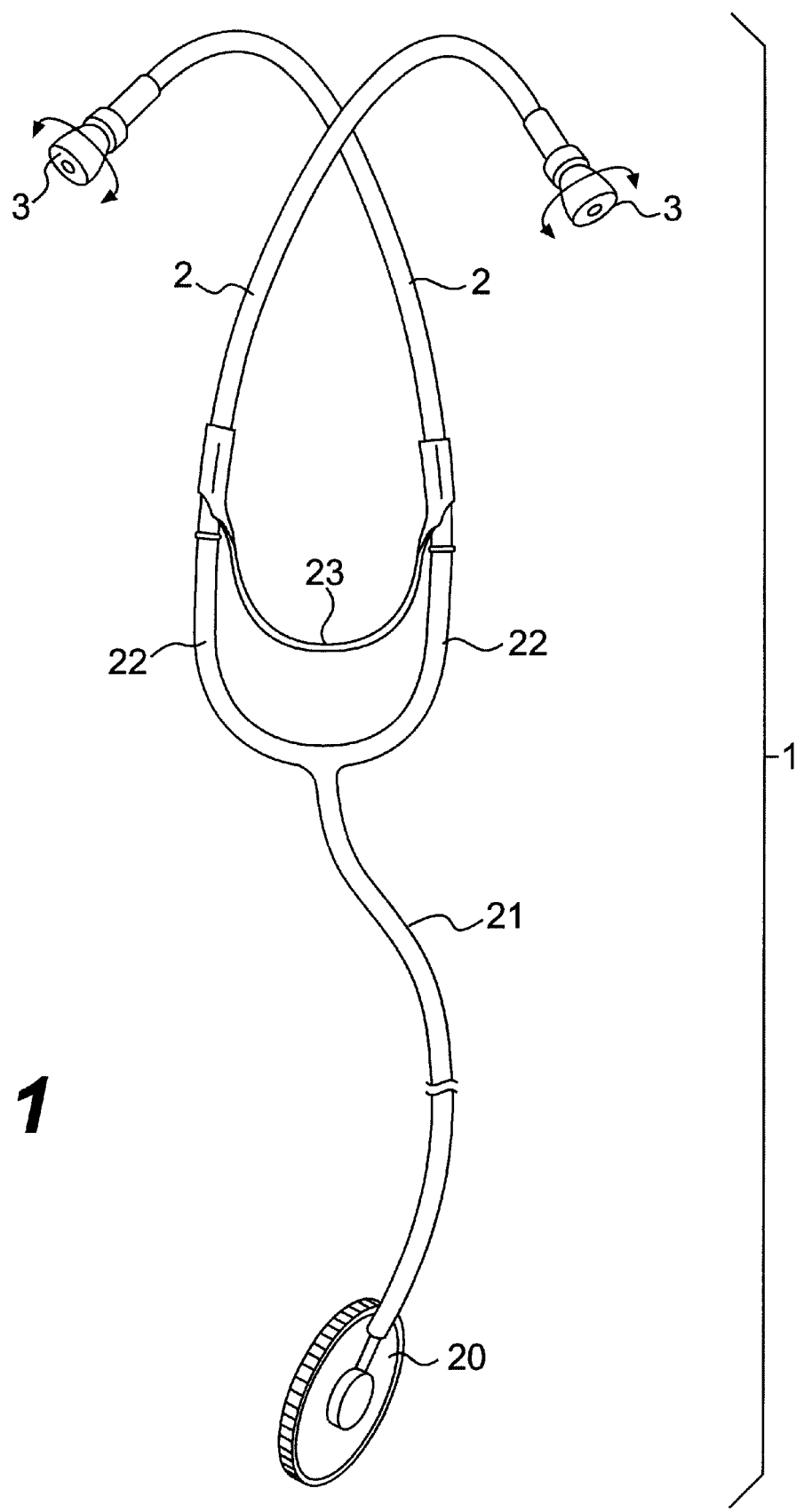
FIG. 1 is a stethoscope having an earpiece assembly according to the present invention.

In the embodiment illustrated in FIG. 1, a stethoscope, generally designated by the reference numeral 1, is shown to include a sound-receiving portion 20. A stethoscope user places sound-receiving portion 20 against the body of a patient to listen physiological sounds, such as heart and respiratory sounds, of the patient. Sound-receiving portion 20 has a diaphragm member and is acoustically connected to the distal end of a tubular transmission member 21. Tubular transmission member 21 is preferably made of an elastic material, such as rubber and resin. Tubular transmission member 21 bifurcates into two separate bifurcated transmission portions 22. Stethoscope 1 also includes a pipe member 2 acoustically connected to the proximal end of each of bifurcated transmission portions 22, and an earpiece assembly 3 is attached to each of pipe members 2 at the proximal end. Stethoscope 1, moreover, has a bridge member 23 attached near the distal end of pipe member 2. Bridge member 23 is preferably biased to prevent pipe members 2 from spreading too wide and to keep the earpieces of stethoscope 1 in the user's ear during the operation. Stethoscope 1 has a common sound path extending from sound-receiving portion 20 to earpiece assembly 3. Sounds received at sound-receiving portion 20 travel through the common sound path to earpiece assembly 3 and to the user's ear.

Figure 2:
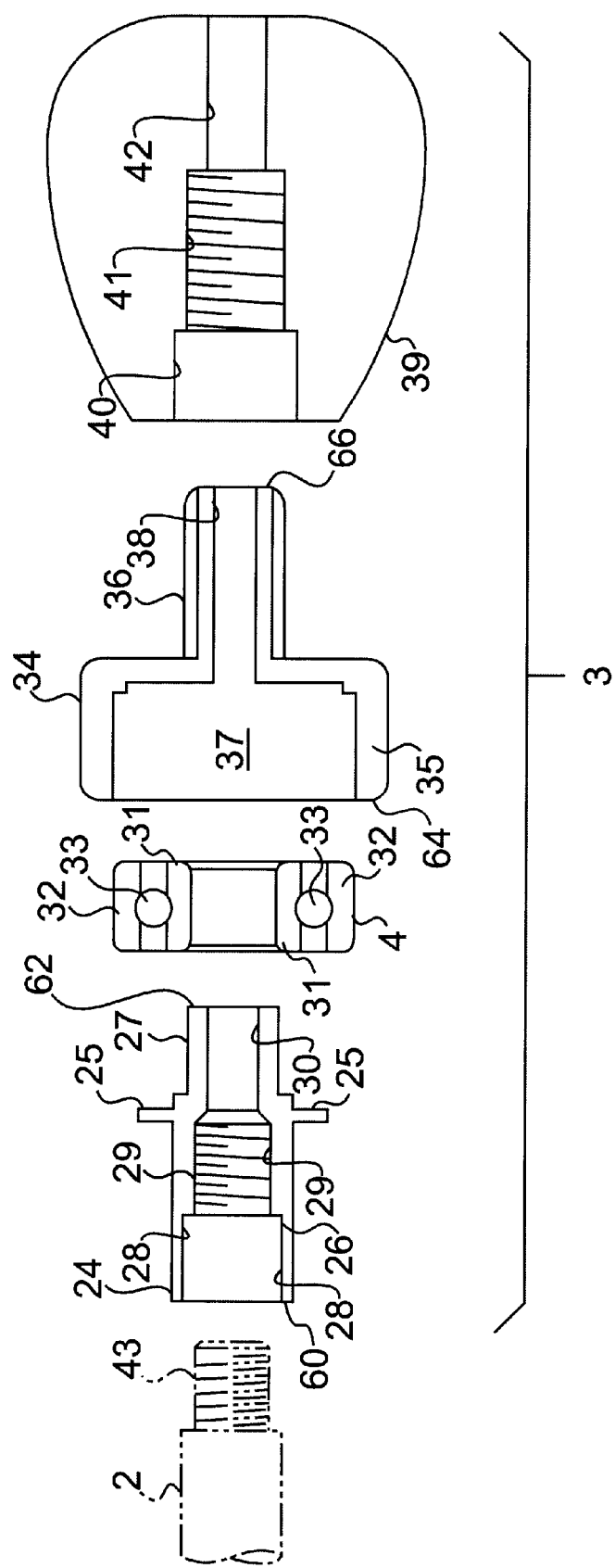
FIG. 2 is an exploded view of the earpiece assembly of FIG. 1.
Figure 3:
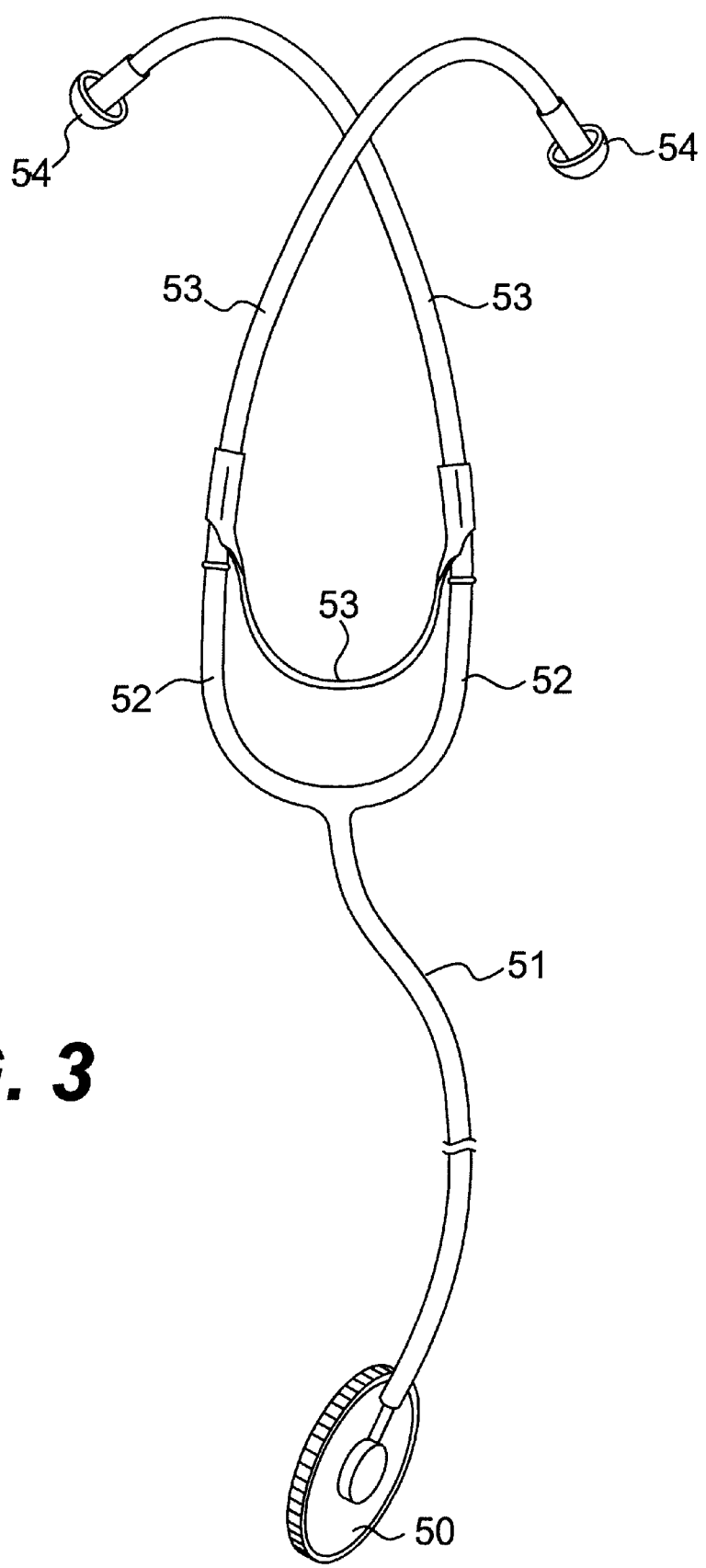
FIG. 3 is a conventional stethoscope.
Figure 4:
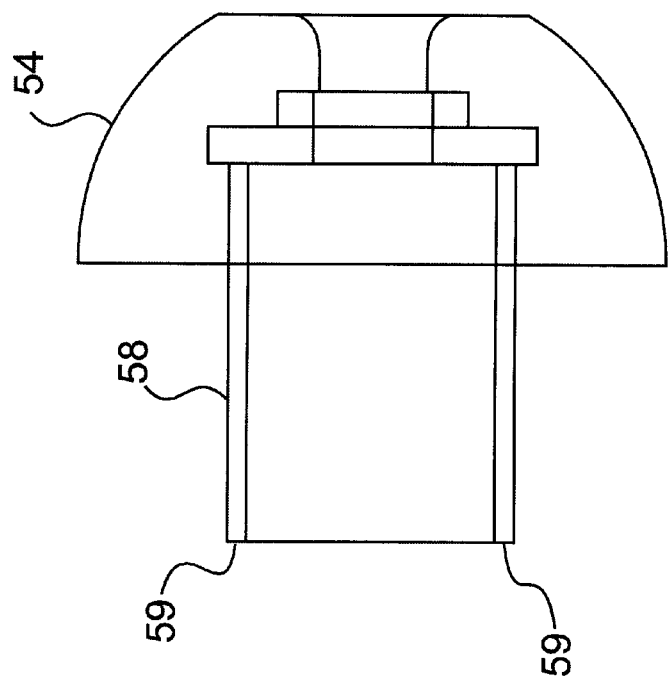
FIG. 4 is an exploded view of an earpiece assembly of the stethoscope shown in FIG. 3.
Figure 4:
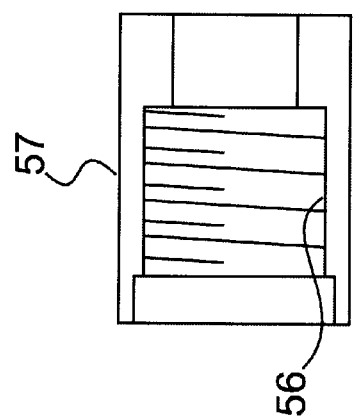
Figure 4:
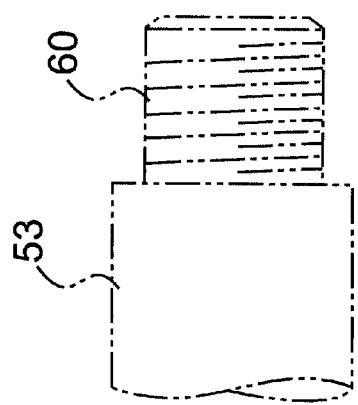
Figure 5:
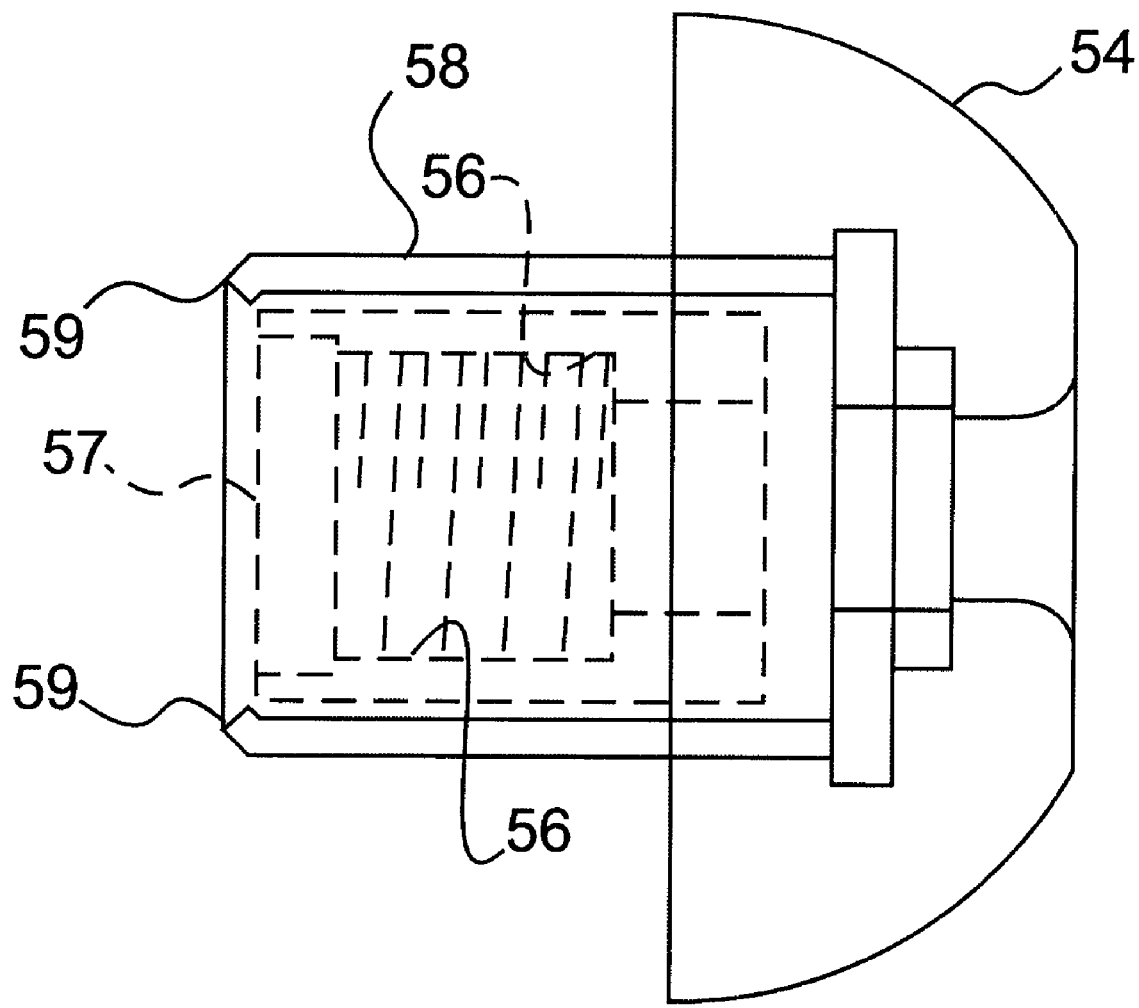
FIG. 5 is a side view of the earpiece assembly of FIG. 4 connected to a pipe member.

As illustrated in FIG. 2, earpiece assembly 3 includes a connector 24, a bushing 34, and an earpiece 39. Connector 24 is preferably made of a metal, and has a distal end 60 and a proximal end 62. In on preferred embodiment, connector 24 has a flange 25 around its outer circumference. A distal connection portion 26 is formed between flange 25 and distal end 60 of connector 24, and a proximal connection portion 27 is formed between flange 25 and proximal end 62 of connector 24. Connector 24 has an opening at distal end 60 for being coupled to pipe member 2. Preferably, distal connection portion 26 includes an insertion hole 28 and a screw hole 29 having teeth to be acoustically coupled to a screw portion 43 of pipe member 2. Proximal connection portion 27 has an aperture 30 at proximal end 62. Insertion hole 28, screw hole 29 and aperture 30 of connector 24 form a part of the common sound path of earpiece assembly 3.

In one preferred embodiment, earpiece assembly 3 includes a bearing 4 for rotatably coupling connector 24 and bushing 34. In an example shown in FIG. 2, bearing 4 is a ball bearing having balls 33 placed between an inner journal 31 and an outer journal 32 to allow free and independent rotation of inner journal 31 and outer journal 32. Though a ball bearing is used in this example, a bearing of different types may be used. Bearing 4 is preferably coupled to proximal connection portion 27 of connector 24.

As illustrated in FIG. 2, bushing 34 has a distal end 64 and a proximal end 66. Preferably, bushing 34 is made of hard resin, and has an open flange portion 35 at distal end 64 and a protrusion 36 at proximal end 66. Open flange portion 35 may have an opening 37 configured to contain bearing 4. When bearing 4 is placed in opening 37, outer journal 32 of bearing 4 is covered by open flange portion 35. Protrusion 36 has screw teeth 36 formed on its outer surface for acoustic coupling with earpiece 39. Protrusion 36 also has an aperture 38 that forms a part of the sound path of stethoscope 1.

Earpiece assembly 3 furthermore includes earpiece 39. Earpiece 39 is preferably made of hard resin and should be shaped to fit into a user's ear. Earpiece 39 has a proximal opening 40, a screw hole 41, and an exit aperture 42, which form a part of the sound path of stethoscope 1. In one preferred embodiment, protrusion 36 of bushing 34 is screwed into earpiece 39 from distal opening 40 and secured to screw hole 41.

Earpiece assembly 3 shown in FIG. 2 may be assembled by the following steps:

(1) Proximal connection portion 27 of connector 24 is coupled into bearing 4, and proximal connection portion 27 and inner journal 31 of bearing 4 should be coupled in a pressure tight manner;

(2) Protrusion 36 of bushing 34 is coupled into distal opening 40 of earpiece 39 by screwing protrusion 36 into screw hole 41 of earpiece 39;

(3) Bearing 4 attached to connector 24 is coupled into opening 37 of bushing 34, and outer journal 32 of bearing 4 and bushing 34 should be coupled in a pressure-tight manner;

(4) screw portion 43 of pipe member 2 is coupled to distal connection portion 26 of connector 24 by screwing screw portion 43 into screw hole 29 of connector As a result of this assembly, connector 24 and bushing 34 are rotatably coupled via bearing 4, and earpiece 4 and pipe member 2 should be freely and independently rotatable.

It will be apparent to those skilled in the art that various modifications and variations can be made in the earpiece assembly or the stethoscope of the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An earpiece assembly for use in a stethoscope having a pipe member, comprising:
    a connector having a distal end and a proximal end;
    a bushing having a distal end rotatably coupled to the proximal end of the connector and a proximal end;
    a bearing for rotatably coupling the connector and the bushing, the bearing having an outer member coupled to the bushing, an inner member coupled to the connector, and a plurality of balls disposed between the outer and inner members; and
    an earpiece having a sound path and being coupled to the proximal end of the bushing.

2. The earpiece assembly of claim 1, wherein the connector, the bushing, and the earpiece are accoustically coupled together to define a common sound path extending though the earpiece assembly.

3. The earpiece assembly of claim 1, wherein the bearing is coupled to the proximal end of the connector and the distal end of the bushing.

4. The earpiece assembly of claim 1, wherein the bushing has a distal opening for accommodating the bearing.

5. The earpiece assembly of claim 1, wherein the connector has a flange at an outer surface thereof.

6. The earpiece assembly of claim 1, wherein the connector has an opening at the distal end of the connector for being coupled to the pipe member.

7. The earpiece assembly of claim 6, wherein the connector is adapted to be coupled to the pipe member by being screwed onto the pipe member.

8. The earpiece assembly of claim 1, wherein the bushing is coupled to the earpiece by being screwed into the earpiece.

9. The earpiece assembly of claim 8, wherein the earpiece having a proximal opening.

10. A stethoscope, comprising:
   a sound-receiving portion;
   a tubular member acoustically coupled to the sound-receiving portion;
   an earpiece assembly acoustically coupled to the tubular member, the earpiece assembly including:
      a connector having a distal end coupled to a pipe member and a proximal end;
      a bushing having a distal end rotatably coupled to the proximal end of the connector and a proximal end;
      a bearing for rotatably coupling the connector and the bushing, the bearing having an outer member coupled to the bushing, an inner member coupled to the connector, and a plurality of balls disposed between the outer and inner members; and
   an earpiece having a sound path and being coupled to the proximal end of the bushing.

11. The stethoscope of claim 10, wherein the sound-receiving portion, the tubular member, and the earpiece assembly are accoustically coupled together to define a common sound path extending though the stethoscope.

12. The stethoscope of claim 10, wherein the tubular member is bifurcated into bifurcated portions.

13. The stethoscope of claim 12, further including the pipe member acoustically coupled to each of the bifurcated portions of the tubular member and the earpiece assembly.

14. The stethoscope of claim 13, further including a bridge member attached to the pipe member.

* * * * *